US008389754B2

(12) United States Patent
Arimoto et al.

(10) Patent No.: US 8,389,754 B2

(45) Date of Patent: Mar. 5, 2013

(54) FRACTIONATION METHOD OF 1,3-DISATURATED-2-UNSATURATED TRIGLYCERIDE

(75) Inventors: Shin Arimoto, Yokosuka (JP); Hidetaka Uehara, Yokosuka (JP); Tomomi Suganuma, Yokosuka (JP); Kinya Tsuchiya, Chuo-ku (JP); Satoshi Negishi, Yokosuka (JP)

(73) Assignee: The Nisshin OilliO Group, Ltd., Tokyo (JP)

( * ) Notice: Subject to any disclaimer, the term of this patent is extended or adjusted under 35 U.S.C. 154(b) by 256 days.

(21) Appl. No.: 12/676,809

(22) PCT Filed: Sep. 8, 2008

(86) PCT No.: PCT/JP2008/066173
§ 371 (c)(1),
(2), (4) Date: Mar. 5, 2010

(87) PCT Pub. No.: WO2009/031680
PCT Pub. Date: Mar. 12, 2009

(65) Prior Publication Data

US 2010/0222607 A1 Sep. 2, 2010

(30) Foreign Application Priority Data

Sep. 7, 2007 (JP) ................................ 2007-232567
Mar. 4, 2008 (JP) ................................ 2008-053465

(51) Int. Cl.
*C07C 51/43* (2006.01)

(52) U.S. Cl. ........................................................ 554/221

(58) Field of Classification Search .................. 554/211
See application file for complete search history.

(56) References Cited

U.S. PATENT DOCUMENTS

| | | | | |
|---|---|---|---|---|
| 4,004,041 | A | 1/1977 | Koslowsky | |
| 4,268,527 | A | 5/1981 | Matsuo et al. | |
| 4,594,259 | A * | 6/1986 | Baker et al. | 426/613 |
| 4,795,569 | A | 1/1989 | Higuchi et al. | |
| 4,985,358 | A | 1/1991 | Sawamura et al. | |
| 5,045,243 | A | 9/1991 | Kuwabara et al. | |
| 6,060,028 | A | 5/2000 | Yoneda et al. | |
| 6,069,263 | A | 5/2000 | Yoneda et al. | |
| 6,969,771 | B2 | 11/2005 | Okada et al. | |
| 2004/0152908 | A1 | 8/2004 | Okada et al. | |
| 2006/0165867 | A1 | 7/2006 | Kuwabara et al. | |
| 2007/0160739 | A1 | 7/2007 | Kuwabara et al. | |

FOREIGN PATENT DOCUMENTS

| | | | |
|---|---|---|---|
| EP | 1 028 159 | A1 | 8/2000 |
| JP | 55-71797 | A | 5/1980 |
| JP | 60-395 | B2 | 1/1985 |
| JP | 62-61589 | A | 3/1987 |
| JP | 63-258995 | A | 10/1988 |
| JP | 2-80495 | A | 3/1990 |
| JP | 3-69516 | B2 | 11/1991 |
| JP | 6-9465 | B2 | 2/1994 |
| JP | 6-181686 | A | 7/1994 |
| JP | 7-49592 | B2 | 5/1995 |
| JP | 7-155107 | A | 6/1995 |
| JP | 7-81156 | B2 | 8/1995 |
| JP | 7-98956 | B2 | 10/1995 |
| JP | 11-80776 | A | 3/1999 |
| JP | 11-246893 | A | 9/1999 |
| JP | 2002-69484 | A | 3/2002 |
| JP | 2003/000832 | A1 | 1/2003 |
| JP | 2004-123839 | A | 4/2004 |
| JP | 3588902 | B2 | 8/2004 |
| WO | WO 96/10643 | A1 | 4/1996 |
| WO | WO 03/000832 | A1 | 1/2003 |
| WO | WO 2004/029185 | A1 | 4/2004 |
| WO | WO 2005/063952 | A1 | 7/2005 |

OTHER PUBLICATIONS

Spear, S. K., et al..: "Renewable plant, based soybean oil methyl esters as alternatives to organic solvents", Green Chemistry, vol. 9, May 24, 2007, pp. 1008-1015.*

Spear et al., "Renewable Plant-based Soybean Oil Methyl Esters as Alternatives to Organic Solvents," Green Chemistry, May 24, 2007, vol. 9, pp. 1008-1015, Royal Society of Chemistry, Cambridge, ISSN: 1463-9262, XP-.

S. Wildes, "Methyl Soyate: A New Green Alternative Solvent," Chemical Health and Safety of the American Chemical Society, May/Jun. 2002, pp. 24-26, American Chemical Society, Washington, DC, ISSN: 1074-9098, XP-002660058.

Extended Search Report from European Patent Office issued in corresponding European Patent Application No. 11168993.1 dated Oct. 21, 2011.

Extended Search Report from European Patent Office issued in corresponding European Patent Application No. 11168989.9 dated Oct. 21, 2011.

International Search Report (PCT/ISA/210) dated Oct. 7, 2008 corresponds to PCT/JP2008/066172.

(Continued)

*Primary Examiner* — Deborah D Carr

(74) *Attorney, Agent, or Firm* — Buchanan Ingersoll & Rooney PC

(57) ABSTRACT

The present invention discloses a method of producing triglycerides rich in XOX fat and/or XLX fat, which comprises the steps of heating and dissolving triglycerides (XOX fat and/or XLX fat) which comprise 20 to 60 mass % of a triglyceride having a saturated fatty acid residue on each of the first and third position and an oleoyl group and/or a linoleoyl group on the second position in total triglycerides in the presence of 1 to 30 mass % of a fatty acid lower alkyl ester; and then cooling the mixture to precipitate crystals and conducting solid-liquid separation. This method is a more efficient and industrially suitable fractionation and production method of fats and oils which are rich in a triglyceride (XOX fat and/or XLX fat) having a saturated fatty acid residue on each of the first and third position and an oleoyl group and/or a linoleoyl group on the second position.

12 Claims, No Drawings

OTHER PUBLICATIONS

Written Opinion (PCT/ISA/237) dated Oct. 7, 2008 corresponds to PCT/JP2008/066172.

International Search Report (PCT/ISA/210) dated Dec. 16, 2008 corresponds to PCT/JP2008/066173.

Written Opinion (PCT/ISA/237) dated Dec. 16, 2008 corresponds to PCT/JP2008/066173.

Translation of the Written Opinion of the International Searching Authority issued in PCT/JP2008/066172 (Mar. 26, 2010).

* cited by examiner

FRACTIONATION METHOD OF 1,3-DISATURATED-2-UNSATURATED TRIGLYCERIDE

TECHNICAL FIELD OF THE INVENTION

The present invention relates to fractionation and production methods of fats and oils which are rich in a triglyceride (XOX fat) having a saturated fatty acid residue on each of the first and third positions and an oleoyl group on the second position; and particularly, it relates to fractionation and production methods of hard butter which has good quality as a cacao butter equivalent (CBE). The present invention also relates to fractionation and production methods of fats and oils which are rich in a triglyceride (XLX fat) having a saturated fatty acid residue on each of the first and third positions and a linoleoyl group (a linoleic acid residue) on the second position; and particularly, it relates to fractionation and production methods of hard butter which has good quality as a chocolate tempering agent.

BACKGROUND OF THE INVENTION

Hard butter including cacao butter is widely used in foods such as confectionery products involving chocolates and bread products, pharmaceutical products, cosmetics, or the like. The above hard butter consists primarily of triglycerides having one unsaturated bond in a molecule such as 1,3-dipalmitoyl-2-oleoyl-glycerol (POP), a triglyceride having an oleoyl group on the second position and each one group of a palmitoyl group and a stearoyl group (POS), and 1,3-distearoyl-2-oleoyl-glycerol (SOS). Further, triglycerides having two unsaturated bonds in a molecule such as 1,3-distearoyl-2-linoleoyl glycerol (SLS) which has good quality as a chocolate tempering agent are also known.

Generally, these triglycerides can be obtained as natural fats and oils containing such compound(s), e.g. palm oil, shea butter, sal fat, and illipe butter; or as fractionated oils thereof.

Further, other than the triglycerides obtained as fractionated oil of fats and oils such as palm oil, shea butter, sal fat, and illipe butter, it is proposed that such triglycerides can also be obtained by the method which comprises the steps of reacting 1,3-selective lipase to specific fats and oils; and transesterifing them to produce the triglycerides (Patent Literatures 1 to 5).

In each of the above methods, fractionation is conducted to obtain an end product (Patent Literatures 6 to 16). However, it has been desired to provide more effective and more industrially suitable fractionation and production methods of fats and oils which are rich in a triglyceride (XOX fat) having a saturated fatty acid residue on each of the first and third positions and an oleoyl group on the second position.

Patent Literature 1: JP-A 55-071797
Patent Literature 2: JP-B 03-069516
Patent Literature 3: JP-B 06-009465
Patent Literature 4: WO96/10643
Patent Literature 5: WO03/000832
Patent Literature 6: WO2005/063952
Patent Literature 7: WO2004/029185
Patent Literature 8: JP-B 01338696
Patent Literature 9: JP-B 02013113
Patent Literature 10: JP-B 02042375
Patent Literature 11: JP-A 63-258995
Patent Literature 12: JP-B 02056898
Patent Literature 13: JP-A 02-080495
Patent Literature 14: JP-B 03588902
Patent Literature 15: JP-A 11-080776
Patent Literature 16: JP-A 2004-123839

DISCLOSURE OF THE INVENTION

The object of the present invention is to provide a more effective and industrially suitable fractionation and production method of fats and oils which are rich in a triglyceride (XOX fat) having a saturated fatty acid residue on each of the first and third positions and an oleoyl group on the second position.

The further object of the present invention is to provide a more effective and industrially suitable fractionation and production method of fats and oils which are rich in a triglyceride (XLX fat) having a saturated fatty acid residue on each of the first and third positions and a linoleoyl group (a linoleic acid residue) on the second position.

The additional object of the present invention is to provide a method of producing XOX fat whose purity is high.

The additional object of the present invention is to provide an industrially suitable method of producing hard butter which has excellent characteristics as CBE of cacao butter.

The further additional object of the present invention is to provide a method of effectively producing a fat and oil composition which comprises less content of a triglyceride consisting of saturated fatty acid residues only or a diglyceride consisting of saturated fatty acid residues only.

The present invention has been completed based on the finding that the above problems can be solved by a method which comprises the steps of heating and dissolving triglycerides comprising a specific amount of XOX fat and/or XLX fat in the presence of a specific amount of a fatty acid lower alkyl ester; and cooling the mixture to precipitate crystals.

The present invention has also been completed based on the finding that the above problems can be solved by a method which comprises the steps of heating and dissolving triglycerides comprising a specific amount of XOX fat and/or XLX fat in the presence of a specific amount of a fatty acid lower alkyl ester; and cooling the mixture with stirring to precipitate crystals.

The present invention has also been completed based on the finding that triglycerides wherein the concentration of XOX fat and/or XLX fat is further increased can be obtained by a method which comprises the steps of adding a specific amount of a fatty acid lower alkyl to solid triglycerides which are rich in XOX fat and/or XLX fat, and crushing the mixture; and then filtering the mixture by compressing to obtain a solid content thereof.

The present invention has also been completed based on the finding that the above problems can be solved by a method which comprises the steps of heating and dissolving a specific amount of triglycerides which comprise XOX fat and/or XLX fat in the presence of a specific amount of a fatty acid lower alkyl ester; and then cooling the mixture, and removing by crystallization a triglyceride (XXX fat) which consists of saturated fatty acid residues only and/or a diglyceride (XX) which consist of saturated fatty acid residues only; and then further crystallizing the reactant.

Namely, the present invention provides a method of producing triglycerides rich in XOX fat, which comprises the steps of heating and dissolving triglycerides which comprise 20 to 60 mass % of a triglyceride (XOX fat) having a saturated fatty acid residue on each of the first and third positions and an oleoyl group on the second position in total triglycerides in the presence of 1 to 30 mass % of a fatty acid lower alkyl ester; and then cooling the mixture to precipitate crystals and conducting solid-liquid separation.

The present invention also provides a method of producing triglycerides rich in XLX fat, which comprises the steps of heating and dissolving triglycerides (XLX fat) which comprise 20 to 60 mass % of a triglyceride having a saturated fatty acid residue on each of the first and third positions and a linoleoyl group on the second position in total triglycerides in the presence of 1 to 30 mass % of a fatty acid lower alkyl ester;

and then cooling the mixture to precipitate crystals and conducting solid-liquid separation.

The present invention also provides a method of producing a triglyceride wherein the concentration of XOX fat and/or XLX fat is further increased, which comprises the steps of adding 1 to 50 parts by weight of a fatty acid lower alkyl ester per 100 parts by weight of the crystals before solid-liquid separation in the above production method, and crushing the mixture; or crushing said crystals and then adding said fatty acid lower alkyl ester thereto; and then filtering the mixture by compressing to obtain a solid content thereof.

The present invention also provides a method of producing triglycerides wherein the concentration of XOX fat and/or XLX fat is increased, which comprises the steps of crushing solid triglycerides rich in XOX fat and/or XLX fat after adding thereto 1 to 50 parts by weight of a fatty acid lower alkyl ester per 100 parts by weight of said solid triglycerides; or crushing the triglycerides before the addition thereof; and then filtering the mixture by compressing to obtain a solid content thereof.

The present invention also provides a method of producing triglycerides wherein the concentration of XOX fat and/or XLX fat is increased, and less XXX fat and XX diglyceride exist, which comprises the steps of heating and dissolving triglycerides which comprise 20 to 60 mass % of XOX fat and/or XLX fat in total triglycerides in the presence of 1 to 30 mass % of a fatty acid lower alkyl ester; and then cooling the mixture and removing by crystallization XXX fat and/or XX diglyceride; and further cooling the reactant with stirring to crystallize XOX fat and/or XLX, and conducting solid-liquid separation.

The present invention also provides a method of producing fats and oils wherein the concentration of XXX fat and/or XX diglyceride is decreased, which comprises the steps of heating and dissolving triglycerides which comprise 20 to 60 mass % of XOX fat and/or XLX fat in total triglycerides in the presence of 1 to 30 mass % of a fatty acid lower alkyl ester; and then cooling the mixture and removing by crystallization a triglyceride (XXX fat) which consists of saturated fatty acid residues only and/or a diglyceride (XX) which consist of saturated fatty acid residues only.

According to the present invention, a more stable crystal polymorphism (β form in the case of XOX fat) can be obtained by making a fatty acid lower alkyl ester exist to triglycerides comprising a specific amount of XOX fat and/or XLX fat as compared with the crystal polymorphism which is obtained in the absence of a fatty acid lower alkyl ester (γ form or β' form in the case of XOX fat). Therefore, there are advantages it is possible to shorten the time for crystallization of fats and oils which are rich in XOX fat (or XLX fat); and, each of stability and the yield of a solid content thereof obtained by crystallization is improved. Further, since crystals of the more stable crystal polymorphism easily grow and harden, it is possible to obtain crystals whose filterability is high and to improve flowability. Particularly, when crystallization is conducted with stirring, flowability significantly improves, and not only does it become easy to pour a solution into a compress filter but also does it improve the purity of XOX fat and/or XLX fat. Further, the fragmentation efficiency of the solid crystallization cake is improved. In addition, the flowability of the crystallization cake significantly improves due to the presence of a fatty acid lower alkyl ester before the filtration by compressing, and not only does it become easier to pour a solution into a press filter but also does the ratio of the fatty acid lower alkyl ester in a liquid part which exists in the obtained solid part increase. It is further possible to obtain the advantage that the purity of XOX fat and/or XLX fat in fats and oils improves by removing the fatty acid lower alkyl ester after that. Besides, XXX fat and XX diglyceride each of which adversely affects crystals of chocolates can be removed by crystallizing XOX fat after removing XXX fat and XX diglyceride. In addition to it, it also has the advantage that crystals of XOX fat and/or XLX fat having good filterability can be prepared and the purity of XOX fat and/or XLX fat improves. Therefore, the production method of the present invention can be extremely preferably used as the fractionation method of hard butter which has good quality as a cacao butter equivalent (CBE).

Further, it is possible to effectively produce fat and oil compositions which contain less content of a triglyceride consisting of saturated fatty acid residues only or a diglyceride consisting of saturated fatty acid residues only by using the arts of the present invention. Thus, defogging property of the fat and oil compositions improves and, particularly, it is possible to effectively produce cooking oil or the like having good low-temperature property.

BEST MODE FOR CARRYING OUT THE INVENTION

In triglycerides which comprise 20 to 60 mass % of a triglyceride (XOX fat and/or XLX fat) having a saturated fatty acid residue on each of the first and third positions and an oleoyl group and/or a linoleoyl group on the second position in total triglycerides, saturated fatty acid residues are preferably those having 16 to 22 carbon atoms; more preferably a stearoyl group, palmitoyl group or behenoyl group; and particularly preferably a stearoyl group on each of the first and third positions.

Triglycerides used in the present invention preferably comprise 30 to 60 mass % (and further 35 to 55 mass %) of XOX fat, and particularly preferably 30 to 50 mass % of SOS; 20 to 50 mass % of SOO; and 3 to 15 mass % of OOO. Here, S indicates a stearoyl group, and O indicates an oleoyl group.

Triglycerides used in the present invention may be distillation residues obtained by transesterifying a triglyceride having an oleoyl group on the second position with a fatty acid lower alkyl ester (including the case of using a fatty acid itself) and then distilling it. More specifically, they can be obtained by the method which comprises the steps of adding a fatty acid lower alkyl ester to raw fats and oils such as trioleoylglycerol, low-melting-point part of shea butter (for example, iodine value 70 to 80), high-oleic sunflower oil, high-oleic low-linolenic canola oil, high-oleic safflower oil, palm oil and palm fractionation oil; further acting 1,3-selective lipase such as *Rhizopus* lipase, *Aspergillus* lipase, *Mucor* lipase, pancreatic lipase and rice bran lipase to conduct transesterification; and then distilling the reactant and removing an unreacting raw material, by-product fatty acids such as an oleic acid or the lower alkyl esters thereof.

Fatty acid lower alkyl esters herein used are preferably lower alcohol esters of saturated fatty acids having 16 to 22 carbon atoms, and particularly preferably esters with alcohols having 1 to 6 carbon atoms. Particularly, methanol, ethanol or isopropyl alcohol is preferable, and ethanol is further more preferable among them.

The usage rate (molar ratio) of a triglyceride having an oleoyl group on the second position per a fatty acid lower alkyl ester is preferably 1/2 or less, and particularly preferably 1/2 to 1/30.

In triglycerides which comprise 20 to 60 mass % of a triglyceride (XLX fat) having a saturated fatty acid residue on each of the first and third positions and a linoleoyl group on the second position, saturated fatty acid residues are preferably those having 16 to 22 carbon atoms; more preferably a stearoyl group, palmitoyl group or behenoyl group; and particularly preferably a stearoyl group on each of the first and third positions.

Triglycerides used in the present invention preferably comprise 30 to 60 mass % (and further 35 to 55 mass %) of XLX fat, and particularly preferably 30 to 50 mass % of SLS; 20 to 50 mass % of SLL; and 3 to 15 mass % of LLL. Here, S indicates a stearoyl group, and L indicates a linoleoyl group.

XLX fat can be produced by the same method as that of XOX fat except that a triglyceride having a linoleoyl group on the second position is used instead of a triglyceride having an oleoyl group on the second position.

1,3-Selective lipase is preferably *Rhizopus delemar* or *Rhizopus oryzae* of *Rhizopus* sp.

Examples of these lipases include Picantase R8000 (a product of Robin) and Lipase F-AP 15 (a product of Amano Enzyme Inc.). The most preferable lipase is Lipase DF "Amano" 15-K (also referred to as Lipase D) derived from *Rhizopus oryzae*, a product of Amano Enzyme Inc. This product is a powdered lipase. Meanwhile, DF "Amano" 15-K was previously described as it is derived from *Rhizopus delemar.*

Lipases herein used may be those obtained by drying an aqueous solution of lipase which contains the medium component of the lipase, or the like. As powdered lipases, it is preferable to use those which is spherical and of which water content is 10 mass % or less. It is particularly preferable to use a powdered lipase of which 90 mass % or more have a particle size of 1 to 100 μm. It is also preferable to use a powdered lipase which is produced by the method comprising the step of spray drying an aqueous solution of lipase of which pH is adjusted to 6 to 7.5.

It is also preferable to use a granulated powdered lipase (also referred to as a powdered lipase) which is produced by the method comprising the steps of granulating the above lipase with soybean powder and powderizing it.

As soybean powder herein used, it is preferable to use those wherein the fat content is 5 mass % or more. As the soybean powder wherein the fat content is 5 mass % or more, it is further preferable that the fat content therein is 10 mass % or more, and it is further more preferable that it is 15 mass % or more. On the other hand, it is preferable that the fat content therein is 25 mass % or less. Particularly, soybean powder wherein the fat content is 18 to 23 mass %.

Examples of fats include fatty acid triglycerides and analogs thereof. The fat content of soy beans can be easily measured by the method such as Soxhlet extraction and the like.

As such soybean powder, it is possible to use whole fat soy bean powder. It is also possible to use soy milk as a raw material of soybean powder. Soybean powder can be produced by crushing soy beans in accordance with the ordinary method, and the particle size thereof is preferably around 0.1 to 600μm. The particle size thereof can be measured by the same method as that of the particle size of a powdered lipase.

The usage amount of soybean powder per lipase is preferably 0.1 to 200 times by mass standard, more preferably 0.1 to 20 times, and most preferably 0.1 to 10 times.

As for a powdered lipase, the water content thereof is preferably 10 mass % or less, and particularly preferably 1 to 8 mass %. The particle size of a powdered lipase can be optional, and 90 mass % or more of a powdered lipase preferably have a particle size of 1 to 100 μm. The average particle size thereof is preferably 10 to 80 μm. Further, it is preferable that the form of a powdered lipase is spherical.

The particle size of a powdered lipase can be measured, for example, by using a particle size distribution analyzer (LA-500) of HORIBA, Ltd.

As for transesterification reaction, the reaction can be conducted in accordance with the ordinary method, i.e. by adding the above lipase to a raw material which comprises a triglyceride having an oleoyl group on the second position and/or XLX fat and a saturated fatty acid lower alkyl ester. In such a case, it is preferable to conduct the transesterification reaction in the conditions that 0.01 to 10 parts by weight (preferably 0.01 to 2 parts by weight, and more preferably 0.1 to 1.5 parts by weight) of the lipase per 100 parts by weight of the raw material is added thereto, at 35 to 100° C. (preferably 35 to 80° C., and more preferably 40 to 60° C.), for 0.1 to 50 hours (preferably 0.5 to 30 hours, and more preferably 1 to 20 hours). The reaction is preferably conducted by the batch method. The reaction temperature may be optional only if it is the temperature at which fats and oils, which are reaction substrates, dissolve and have an enzymatic activity. The most suitable reaction time changes depending on the enzyme additive amount, reaction temperature, or the like.

After the transesterification, an unreacting raw material, a by-product oleic acid or the lower alkyl esters thereof are removed by distilling the reactant to obtain triglycerides which comprise 20 to 60 mass % and preferably 30 to 60 mass % of a triglyceride having a saturated fatty acid residue on each of the first and third positions and an oleoyl group on the second position (XOX fat) and/or a linoleoyl group on the second position (XLX fat) in total triglycerides, which are used as a raw material in the present invention.

In the present invention, when conducting transesterification, it is allowed to leave 1 to 30 mass % (preferably 4 to 25 mass %, and more preferably 7 to 23 mass %) of a fatty acid lower alkyl ester in a distillation residue comprising triglycerides which comprise 20 to 60 mass % and preferably 30 to 60 mass % of a triglyceride (XOX fat) having a saturated fatty acid residue on each of the first and third positions and an oleoyl group on the second position (and/or XLX fat) in total triglycerides, by using an excess amount of a fatty acid lower alkyl ester and distilling the reactant. Further, it is also allowed to remove an unreacting raw material (including a fatty acid lower alkyl ester), a by-product oleic acid or the lower alkyl esters thereof as much as possible by distillation; and to newly add a fatty acid lower alkyl ester to triglycerides which comprise 20 to 60 mass % and preferably 30 to 60 mass % of a triglyceride (XOX fat) having a saturated fatty acid residue on each of the first and third positions and an oleoyl group on the second position (and/or XLX fat) in total triglycerides, so that the fatty acid lower alkyl ester becomes 1 to 30 mass % (preferably 4 to 25 mass %, and more preferably 7 to 23 mass %).

A fatty acid lower alkyl esters newly added thereto is not particularly limited, and preferably lower alcohol esters of fatty acids having 16 to 22 carbon atoms, and particularly preferably esters of saturated fatty acids and alcohols having 1 to 6 carbon atoms. Particularly, methanol, ethanol or isopropyl alcohol is preferable, and ethanol is further more preferable among them.

In the present invention, it is preferable to produce triglycerides which are rich in XOX fat by the method which comprises the steps of dissolving thus prepared triglycerides which comprise a specific amount of a fatty acid lower alkyl ester by heating them up to the temperature at which all of them uniformly dissolve (for example, 50° C. or higher, and preferably 50 to 70° C.) keeping the reactant at the same temperature soon after the dissolution or for a specified time (for example, 0.5 to 2 hours); then cooling it down to room temperature or lower (for example, 26° C. or lower, preferably 15 to 26° C., and more preferably 18 to 22° C.) to precipitate a solid content which is rich in XOX fat; and conducting solid-liquid separation to obtain said triglycerides. In addition, it is also preferable to keep the reactant at specific temperature (for example, 26 to 35° C., and preferably 26 to 28° C.) for a specified time (for example, 0.5 to 5 hours, and preferably 1 to 3 hours) before cooling it down to room temperature or lower to precipitate a solid content which is rich in XOX fat. Meanwhile, as for XLX fat, cooling temperature is preferably 20° C. or lower, and more preferably 5 to 15° C.

The above processes from dissolution by heating to cooling can be conducted with stirring and/or still standing. This method makes it possible to obtain triglycerides wherein the content of XOX fat (and/or XLX fat) is 65 mass % or more, and preferably 70 mass % or more. According to the method, especially, it is possible to shorten the time for crystallization of fats and oils which are rich in XOX fat (and/or XLX fat); and, each of stability and the yield of a solid content obtained by crystallization is improved. In addition to it, it also has the advantage that crystals having good filterability can be obtained and the purity of XOX fat (and/or XLX fat) improves. Further, in the method comprising the steps of making a fatty acid lower alkyl ester comprised; and cooling the reactant with stirring, a crystallized substance having flowability can be obtained, and crystals thereof have good filterability. Thus, since it becomes easier to conduct solid-liquid separation, it is possible to obtain the advantage that the content of XOX fat (and/or XLX fat) is increased.

In the present invention, the solid content which is rich in XOX fat (and/or XLX fat) is precipitated by the method comprising the steps of heating and dissolving triglycerides comprising a specific amount of a fatty acid lower alkyl ester, and cooling it down. In such processes, it is preferable to produce triglycerides which are rich in XOX fat (and/or XLX fat) by the method comprising the steps of crystallizing XXX fat or XX diglyceride at the temperature at which XOX fat (and/or XLX fat) hardly crystallizes (for example 26 to 35° C., and preferably 26 to 28° C.), and removing it by separation; then cooling the reactant to room temperature or lower (for example, 25° C. or lower), or heating the reactant again (for example, 50° C. or higher, and preferably 50 to 70° C.) and then cooling it down to room temperature or lower (for example, 25° C. or lower) to precipitate a solid content which is rich in XOX fat (and/or XLX fat); and conducting solid-liquid separation to such solid content to obtain said triglycerides. In addition, it is also preferable to keep the reactant at specific temperature (for example, 26 to 35° C., and preferably 26 to 28° C.) for a specified time (for example, 0.5 to 5 hours, and preferably 1 to 3 hours) after removing XXX fat or XX diglyceride by separation and before cooling the reactant to room temperature or lower to precipitate a solid content which is rich in XOX fat (and/or XLX fat). According to this method comprising the step of making a fatty acid lower alkyl ester comprised, the content of XOX fat (and/or XLX fat) is high, and the stability of the solid content obtained by crystallization is improved. In addition to it, it also has the advantage that XXX fat or XX diglyceride can be decreased, each of which adversely affects crystals of chocolates.

Besides, in the present invention, the intended fats and oils wherein XXX fat or XX diglyceride is decreased by the above method may be separated in accordance with the ordinary method, by using the separation method with a solvent(s) such as acetone. In this separation method with a solvent(s), it is possible to use ethanol or hexane in addition to acetone.

In the present invention, the concentration of XOX fat (and/or XLX fat) can be further increased by the method comprising the steps of adding 1 to 50 parts by weight (preferably 5 to 50 parts by weight, more preferably 10 to 50 parts by weight, and most preferably 15 to 50 parts by weight) of a fatty acid lower alkyl ester per 100 parts by weight of the crystals before solid-liquid separation, and crushing the mixture; or crushing said crystals and then adding said fatty acid lower alkyl ester thereto; and then filtering the mixture by compressing to obtain a solid content.

At that time, it is preferable that the crystals before solid-liquid separation are those obtained by the method comprising the steps of heating and dissolving triglycerides in the presence of 1 to 30 mass % of a fatty acid lower alkyl ester; and then cooling the mixture to precipitate said crystals.

In this method, it is preferable that crushing is conducted in the presence of a fatty acid lower alkyl ester by using, for example, a metallic mesh or a marketed juicer, and at room temperature or lower (preferably 20 to 27° C.), for example. Then, filtration by compressing is preferably conducted with, for example, a press filter which is used for separation by filtration of palm oil or the like and at room temperature or lower (preferably 20 to 27° C.). The purification process, which is an optional process conducted after the above process, can be conducted in accordance with the ordinary method (such as steam distillation). According to this method, a fatty acid lower alkyl ester can be removed before producing an end product. Thus, it is possible to obtain triglycerides wherein the content of XOX fat (and/or XLX fat) is 75 mass % or more, and preferably 80 mass % or more.

Further, it is preferable that, after filtration by compressing to obtain a solid content, a purification process(es) is further conducted such as the process of removing a fatty acid lower alkyl ester in the solid content. It is also allowed to conduct a usually operated purification process(es) of fats and oils such as bleaching and deodorizing.

The fats and oils wherein the content of XOX fat is increased which are obtained by the method of the present invention can be particularly preferably used as hard butter which has good quality as a cacao butter equivalent (CBE). Further, the fats and oils wherein the content of XLX fat is increased which are obtained by the method of the present invention can be particularly preferably used as hard butter which has good quality as a chocolate tempering agent.

Chocolate products comprise a sugar component and a fat and oil component wherein the above hard butter and cacao butter are mixed. It is preferable that the above hard butter is contained in the fat and oil component at a rate of 10 mass % or more, preferably 20 mass % or more, and further more preferably 30 mass %. As for a sugar component, any one which is used for chocolates is usable. Examples thereof include sucrose, fructose, mixture thereof, and the like. Sugar alcohols such as sorbitol is also usable. In addition, other optional component(s) which is usually contained in chocolate products can also be contained. Examples thereof include emulsifying agents (usually, lecithin), flavoring agents, skim milk powder, and whole milk powder.

In the present invention, fats and oils wherein the concentration of XXX fat and/or XX diglyceride is decreased can be produce by the method which comprises the steps of heating and dissolving triglycerides which comprise 20 to 60 mass % (preferably 30 to 60 mass %) of XOX fat and/or XLX fat in total triglycerides in the presence of 1 to 30 mass % of a fatty acid lower alkyl ester; and then cooling the mixture and removing by crystallization a triglyceride (XXX fat) which consists of saturated fatty acid residues only and/or a diglyceride (XX) which consist of saturated fatty acid residues only. This method can be conducted in accordance with the above method which comprises the steps of heating and dissolving triglycerides comprising a specific amount of a fatty acid lower alkyl ester, and cooling it to crystallize a solid content which is rich in XOX fat and/or XLX fat, further comprising the steps of crystallizing XXX fat or XX diglyceride at the temperature at which XOX fat and/or XLX fat hardly crystallizes (for example 26 to 35° C., and preferably 26 to 28° C.), and removing it by separation. Since this method can effectively produce a fat and oil composition which contains less content of XXX fat or XX diglyceride, defogging property of the fat and oil composition improves and, particularly, it is possible to effectively produce cooking oil or the like having good low-temperature property.

Next, Examples will further illustrate the present invention.

EXAMPLES

Preparation of a Powdered Lipase Composition 1

Autoclave sterilization (121° C., 15 mins.) was previously conducted to an enzyme solution (150000 U/mL) of a trade name: Lipase DF "Amano" 15-K (also referred to as Lipase D), a product of Amano Enzyme Inc. A threefold amount of 10% aqueous solution of deodorized whole fat soy bean powder (fat content: 23 mass %; trade name: Alphaplus HS-600, produced by Nisshin Cosmo Foods, Ltd.) cooled down to around room temperature was added thereto with stirring. Then, the mixture was adjusted to pH7.8 by 0.5N NaOH solution, and spray-dried (SD-1000, by Tokyo Rikakikai Co., Ltd.) to obtain a powdered lipase composition 1.

Example 1

1800 g of ethyl stearate (trade name: Ethyl Stearate, by Inoue Perfumery MFG. Co., Ltd.) was mixed with 1200 g of high-oleic sunflower oil (trade name: Olein Rich, by Showa Sangyo Co., Ltd.). 0.5 mass % of the powdered lipase composition 1 was added thereto, and stirred at 40° C. for 7 hours. An enzyme powder was removed by filtration to obtain 2987 g of a reactant 1-1. Thin-film distillation was conducted to 2980 g of the obtained reactant 1-1, and an amount exceeding a specific amount of a fatty acid ethyl was removed at distillation temperature of 140° C. to obtain 1290 g of a distillation residue 1-1 wherein the content of a fatty acid ethyl ester is 8.8 mass % (Table 1). Meanwhile, a fatty acid ethyl ester and TAG composition were analyzed by GLC method.

After 930 g of the distillation residue 1-1 was completed dissolved at 50° C., it was solidified at 25° C. to obtain a cake 1-1. The solid-state crystal polymorphism was measured by XRD. The results are shown in Tables 2 and 3.

320 g of the cake 1-1 was put in a juicer (by Zojirushi Corporation) and crushed. Then, solid-liquid separation was conducted to it by pressure filtration (compression pressure 3.3 $kgf/cm^2$; use of The Nisshin OilliO Group, Ltd. self-produced press filter) to obtain 102 g of a solid part 1-1 and 207 g of a liquid part. The results are shown in Table 4.

Comparative Example 1

Steam distillation was conducted to 360 g of the distillation residue 1-1 obtained in Example 1 at distillation temperature of 200° C. Then, a fatty acid ethyl was removed to obtain 320 g of a distillation residue 1-2 wherein the content of a fatty acid ethyl is a trace amount % (Table 1).

After 320 g of the distillation residue 1-2 was completely dissolved at 50° C., it was solidified at 25° C. to obtain a cake 1-2. The solid-state crystal polymorphism was measured by XRD. The results are shown in Tables 2 and 3.

320 g of the cake 1-2 was put in a juicer (by Zojirushi Corporation) and crushed. Then, solid-liquid separation was conducted to it by pressure filtration (compression pressure 3.3 $kgf/cm^2$; use of The Nisshin OilliO Group, Ltd. self-produced press filter) to obtain 62 g of a solid part 1-2 and 248 g of a liquid part 1-2. The results are shown in Table 4.

TABLE 1

TAG composition analysis results

| TAG composition (%) | Reactant 1-1 | Distillation residue 1-1 (Exam. 1) | Distillation residue 1-2 (Comp. Ex. 1) |
|---|---|---|---|
| $PS_2$ | tr | tr | tr |
| POS | 4.3 | 4.3 | 4.5 |
| $PO_2$ | 1.6 | 1.6 | 1.5 |
| $S_3$ | tr | tr | tr |
| $S_2O$ | 46.4 | 46.4 | 46.4 |
| $SO_2$ | 34.8 | 34.8 | 35.1 |
| $S_2L$ | 2.5 | 2.5 | 2.5 |
| $O_3$ | 6.0 | 6.0 | 6.0 |
| SOL | 3.4 | 3.4 | 3.4 |
| others | 1.0 | 1.0 | 0.6 |

TABLE 1-continued

TAG composition analysis results

| TAG composition (%) | Reactant 1-1 | Distillation residue 1-1 (Exam. 1) | Distillation residue 1-2 (Comp. Ex. 1) |
|---|---|---|---|
| XOX/(XXO + OXX) | 99/1 | 99/1 | 99/1 |
| Fatty acid ethyl content (%) | — | 8.8 | tr |

Note 1)

TAG composition indicates the composition of each triglyceride in all triglycerides.

XOX/(XXO + OXX) indicates a ratio of a triglyceride having a saturated fatty acid residue on each of the first and third positions and a triglyceride having a saturated fatty acid residue on the second position among triglycerides having two saturated fatty acid residues and one oleoyl group. Meanwhile, XOX/(XXO + OXX) was analyzed by HPLC using the column packed with a cation exchange resin in the Ag+ ionic form.

P: palmitic acid residue, S: stearic acid residue, O: oleic acid residue, L: linoleic acid residue, and tr: trace.

Note 2)

The content of a fatty acid ethyl ester indicates a mass % of a fatty acid ethyl ester in all components.

TABLE 2

Cystallization conditions

| time for crystallization (hr) | crystal polymorphism(β form. rate) *1 Example 1 | Comp. Example 1 |
|---|---|---|
| 0 | 0 | 0 |
| 16 | 49.0 | 15.0 |
| 22 | 92.1 | 23.4 |
| 39 | 98.4 | 36.3 |

*1 β formulation rate is a value defined as follows, using a intensity of each d value of X-ray diffraction measurement.

β formulation rate = 4.6 Å intensity/(4.6 Å intensity + 3.8 Å intensity) × 100

TABLE 3

Melting point of a crystallization cake

| | Example 1 | Comp. Example 1 |
|---|---|---|
| Melting point (° C.) *2) | 33.8 | 30.4 |

*2) melting peak top temperature of DSC

TABLE 4

Results of solid-liquid separation

| TAG composition (%) | Example 1 Solid part 1-1 | Example 1 Liquid part 1-1 | Comparative Example 1 Solid part 1-2 | Comparative Example 1 Liquid pard 1-2 |
|---|---|---|---|---|
| $PS_2$ | tr | tr | tr | Tr |
| POS | 4.0 | 2.4 | 4.5 | 4.7 |
| $PO_2$ | 0.8 | 2.2 | 2.2 | 2.5 |
| $S_3$ | tr | tr | tr | tr |
| $S_2O$ | 75.2 | 15.8 | 50.3 | 28.2 |
| $SO_2$ | 12.4 | 56.7 | 26.6 | 45.9 |
| $S_2L$ | 2.8 | 3.4 | 3.2 | 3.4 |
| $O_3$ | 2.5 | 11.3 | 9.6 | 9.2 |
| SOL | 1.0 | 6.8 | 3.5 | 4.8 |
| others | 1.3 | 1.4 | 0.1 | 1.3 |

Note 1)

TAG composition indicates the composition of each triglyceride in all triglycerides.

P: palmitic acid residue,

S: stearic acid residue,

O: oleic acid residue,

L: linoleic acid residue, and tr: trace.

Example 2

21000 g of ethyl stearate (trade name: Ethyl Stearate, by Inoue Perfumery MFG. Co., Ltd.) was mixed with 14000 g of high-oleic sunflower oil (trade name: Olein Rich, by Showa Sangyo Co., Ltd.). 0.3 mass % of the powdered lipase composition 1 was added thereto, and stirred at 40° C. for 20 hours. An enzyme powder was removed by filtration to obtain 34354 g of a reactant 2-1. Thin-film distillation was conducted to 34300 g of the obtained reactant 2-1, and a fatty acid ethyl was removed from the reactant at distillation temperature of 140° C. to obtain 13714 g of a distillation residue 2-1 wherein the content of a fatty acid ethyl is 2.9 mass % (Table 5).

2101 g of ethyl stearate (trade name: Ethyl Stearate, by Inoue Perfumery MFG. Co., Ltd.) was mixed with 11417 g of the obtained distillation residue 2-1 to obtain 13518 g of a crystallization raw material 2-1 wherein the content of a fatty acid ethyl is 18.3 mass %. After 12500 g of the obtained crystallization raw material 2-1 was completely dissolved at 50° C., it was cooled down with stirring at 27° C. for 2.5 hours. Then, solid-liquid separation was conducted to it by pressure filtration (pressure filtration 2, compression pressure 7 kgf/cm$^2$; use of The Nisshin OilliO Group, Ltd. self-produced press filter) to obtain 450 g of a solid part 2-1 and 11859 g of a liquid part 2-1. After 3664 g of the obtained liquid part 2-1 was cooled down with stirring at 27° C. for 2.5 hours, and then at 20° C. for 4 hours, solid-liquid separation was conducted to it by pressure filtration (pressure filtration 3, compression pressure 30 kgf/cm$^2$; use of The Nisshin OilliO Group, Ltd. self-produced press filter) to obtain 1458 g of a solid part 2-2 and 2191 g of a liquid part 2-2 (Tables 5, 7). Steam distillation was conducted to the obtained solid part 2-2 at distillation temperature of 200° C., and, a fatty acid ethyl was removed. Then, it was purified by the book to obtain hard butter 2-1. Chocolates comprising the obtained hard butter 2-1 were evaluated, and there was no problem with viscosity as manufactured, demoulding, or chocolate's melting in the mouth.

Example 3

After 1000 g of the crystallization raw material 2-1 obtained by the method of Example 2 was completely dissolved at 50° C., it was cooled down with stirring at 27° C. for 2.5 hours, and then at 20° C. for 4 hours. Then, solid-liquid separation was conducted to it by pressure filtration (pressure filtration 4, compression pressure 30 kgf/cm$^2$; use of The Nisshin OilliO Group, Ltd. self-produced press filter) to obtain 410 g of a solid part 3-1 and 568 g of a liquid part 3-1 (Tables 5, 8). Steam distillation was conducted to the obtained solid part 3-1 at distillation temperature of 200° C., and, a fatty acid ethyl was removed. Then, it was purified by the book to obtain hard butter 3-1. Chocolates comprising the obtained hard butter 3-1 were evaluated, and they had good quality. Further, chocolates comprising the hard butter 2-1 of Example 2 had low viscosity as manufactured, and the demoulding thereof was slightly better. In addition, chocolates of Example 2 melted better in the mouth.

Example 4

After 4000 g of the liquid part 2-1 obtained by the method of Example 2 was completely dissolved at 50° C., it was cooled down with stirring at 27° C. for 2.5 hours, and then at 20° C. for 4 hours. Then, solid-liquid separation was conducted to it by pressure filtration (pressure filtration 5, compression pressure 30 kgf/cm$^2$; use of The Nisshin OilliO Group, Ltd. self-produced press filter) to obtain 1568 g of a solid part 4-1 and 2352 g of a liquid part 4-1 (Tables 6, 9).

Example 5

After 3000 g of the liquid part 2-1 obtained by the method of Example 2 was completely dissolved at 50° C., it was cooled down with stirring at 27° C. for 2.5 hours, and then cooled down to 20° C. at a speed of 1° C./hour. Then, the reactant was kept at 20° C. for 1 hour, and solid-liquid separation was conducted to it by pressure filtration (pressure filtration 6, compression pressure 30 kgf/cm$^2$; use of The Nisshin OilliO Group, Ltd. self-produced press filter) to obtain 1147 g of a solid part 5-1 and 1793 g of a liquid part 5-2 (Tables 6, 9).

Comparative Example 2

Steam distillation was conducted to 1000 g of the distillation residue 2-1 obtained by the method of Example 2 at distillation temperature of 200° C. Then, a fatty acid ethyl was removed to obtain 982 g of a distillation residue 2-2 wherein the content of a fatty acid ethyl is a trace amount %. After 950 g of the distillation residue 2-2 was completely dissolved at 50° C., it was cooled down with stirring at 27° C. for 3 hours and filtered by compressing (pressure filtration 7, compression pressure 7 kgf/cm$^2$; use of The Nisshin OilliO Group, Ltd. self-produced press filter) to conduct solid-liquid separation. However, the separation was stopped because the viscosity thereof became extremely high and filterability deteriorated so that the solid-liquid separation could not be continued. Therefore, after the reactant was completely dissolved at 50° C. again, it was cooled down with stirring at 27° C. for 2.5 hours, and then at 20° C. for 4 hours. Then, solid-liquid separation was conducted to it by pressure filtration (pressure filtration 8, compression pressure 30 kgf/cm$^2$; use of The Nisshin OilliO Group, Ltd. self-produced press filter). However, the separation was stopped again since it was difficult to conduct the solid-liquid separation due to the low filterability thereof (Tables 5, 8).

TABLE 5

| Flowability before pressure filtration | | | |
|---|---|---|---|
| | Example 2 | | Example 3 |
| | Bfr. press. filt. 2 | Bfr. press. filt. 3 | Bfr. press. filt. 4 |
| flowability | ◎◎ | ◎ | ◎ |

◎◎: Liquid form.
◎: Flowability is extremely high; almost liquid form.
▲: Though having flowability to some extent, viscosity is high and filtration is difficult.

TABLE 6

| Flowability before pressure filtration | | | |
|---|---|---|---|
| | Example 4 Bfr. press. filt. 5 | Example 5 Bfr. press. filt. 6 | Comp. Ex. 2 Bfr. press. filt. 7, 8 |
| flowability | ◎ | ◎ | ▲ |

◎: Flowability is extremely high; almost liquid form.
▲: Though having flowability to some extent, viscosity is high and filtration is difficult.

TABLE 7

Composition analysis results

| TAG composition (%) Note 1) | Example 2 Reactant 2-1 | Distillation residue 2-1 | Crystal. RM 2-1 | Solid part 2-1 | Liquid part 2-1 | Solid part 2-2 | Liquid part 2-2 | Hard butter 2-1 |
|---|---|---|---|---|---|---|---|---|
| $PS_2$ | tr | tr | tr | 1.5 | tr | tr | tr | tr |
| POS | 2.9 | 2.9 | 2.9 | 2.5 | 3.1 | 3.4 | 2.6 | 3.4 |
| $PO_2$ | 1.4 | 1.4 | 1.4 | 1.0 | 1.7 | 0.2 | 3.1 | 0.2 |
| $S_3$ | 0.7 | 0.7 | 0.7 | 15.4 | 0.3 | 0.8 | tr | 0.8 |
| $S_2O$ | 43.7 | 43.7 | 43.7 | 44.1 | 41.7 | 78.6 | 12.1 | 78.6 |
| $SO_2$ | 35.6 | 35.6 | 35.6 | 25.3 | 35.2 | 11.8 | 51.9 | 11.8 |
| $S_2L$ | 2.5 | 2.5 | 2.5 | 1.3 | 2.5 | 1.8 | 3.3 | 1.8 |
| $O_3$ | 7.7 | 7.7 | 7.7 | 5.7 | 9.6 | 1.6 | 18.2 | 1.6 |
| SOL | 4.2 | 4.2 | 4.2 | 2.5 | 3.6 | 1.0 | 5.6 | 1.0 |
| others | 1.3 | 1.3 | 1.3 | 0.7 | 2.3 | 0.8 | 3.2 | 0.8 |
| SS-DAG content (%) Note 2) | 0.4 | 1.1 | 1.0 | 35.0 | 0.2 | 0.5 | tr | 0.6 |
| XOX/(XXO + OXX) | 99/1 | 99/1 | 99/1 | — | 99/1 | 99/1 | — | 99/1 |
| Fatty acid ethyl content (%) Note 3) | — | 2.9 | 18.3 | 12.0 | 18.4 | 11.9 | 20.9 | ND |

Note 1)
TAG composition indicates the composition of each triglyceride in all triglycerides.
XOX/(XXO + OXX) indicates a ratio of a triglyceride having a saturated fatty acid residue on each of the first and third positions and a triglyceride having a saturated fatty acid residue on the second position among triglycerides having two saturated fatty acid residues and one oleoyl group.
P: palmitic acid residue, S: stearic acid residue, O: oleic acid residue, L: linoleic acid residue, and tr: trace.
Note 2)
SS-DAG content indicates a mass % of distearoyl-glycerol in all components. The content was measured by GLC.
Note 3)
The content of a fatty acid ethyl indicates a mass % of a fatty acid ethyl in all components.

TABLE 8

Composition analysis results

| TAG composition (%) Note 1) | Example 3 Solid part 3-1 | Liquid part 3-1 | Hard butter 3-1 | Comp. Ex. 2 Distillation residue 2-2 |
|---|---|---|---|---|
| $PS_2$ | tr | tr | tr | tr |
| POS | 3.5 | 2.7 | 3.5 | 2.9 |
| $PO_2$ | 0.2 | 3.1 | 0.2 | 1.4 |
| $S_3$ | 2.0 | Tr | 2.0 | 0.7 |
| $S_2O$ | 75.1 | 15.0 | 75.1 | 43.7 |
| $SO_2$ | 12.4 | 52.0 | 12.4 | 35.6 |
| $S_2L$ | 2.6 | 3.3 | 2.6 | 2.5 |
| $O_3$ | 2.4 | 18.8 | 2.4 | 7.7 |
| SOL | 0.9 | 5.6 | 0.9 | 4.2 |
| others | 0.5 | 1.7 | 0.5 | 1.3 |
| SS-DAG content (%) Note 2) | 1.9 | tr | 2.1 | 1.2 |
| XOX/(XXO + OXX) | 99/1 | — | 99/1 | 99/1 |
| Fatty acid ethyl content (%) Note 3) | 12.5 | 18.5 | ND | tr |

Note 1)
TAG composition indicates the composition of each triglyceride in all triglycerides.
P: palmitic acid residue,
S: stearic acid residue,
O: oleic acid residue,
L: linoleic acid residue, and
tr: trace.
Note 2)
SS-DAG content indicates a mass % of distearoyl-glycerol in all components. The content was measured by GLC.
Note 3)
The content of a fatty acid ethyl indicates a mass % of a fatty acid ethyl in all components.

TABLE 9

Composition analysis results

| TAG composition (%) Note 1) | Example 4 Solid part 4-1 | Liquid part 4-1 | Example 5 Solid part 5-1 | Liquid part 5-1 |
|---|---|---|---|---|
| $PS_2$ | tr | tr | tr | tr |
| POS | 3.4 | 2.7 | 3.5 | 2.8 |
| $PO_2$ | 0.2 | 3.1 | 0.2 | 3.6 |
| $S_3$ | 0.9 | tr | 1.0 | tr |
| $S_2O$ | 80.2 | 13.4 | 81.2 | 14.2 |
| $SO_2$ | 10.7 | 51.9 | 9.9 | 51.4 |
| $S_2L$ | 2.1 | 3.3 | 2.1 | 3.3 |
| $O_3$ | 1.1 | 18.4 | 0.9 | 18.6 |
| SOL | 0.9 | 5.5 | 0.7 | 5.3 |
| others | 0.5 | 1.7 | 0.5 | 0.8 |
| SS-DAG content (%) Note 2) | 0.6 | tr | 0.6 | tr |
| XOX/(XXO + OXX) | 99/1 | — | 99/1 | — |
| Fatty acid ethyl content (%) Note 3) | 11.8 | 20.7 | 11.6 | 20.5 |

Note 1)
TAG composition indicates the composition of each triglyceride in all triglycerides.
P: palmitic acid residue,
S: stearic acid residue,
O: oleic acid residue,
L: linoleic acid residue, and
tr: trace.
Note 2)
SS-DAG content indicates a mass % of distearoyl-glycerol in all components. The content was measured by GLC.
Note 3)
The content of a fatty acid ethyl indicates a mass % of a fatty acid ethyl in all components.

Example 6

60 g of 31.7° C. liquid ethyl stearate was added to 200 g of the cake 1-1 obtained by the method of Example 1, and the mixture was put in a juicer (by Zojirushi Corporation) and crushed. Then, solid-liquid separation was conducted to it by pressure filtration (compression pressure 3.3 $kgf/cm^2$; use of The Nisshin OilliO Group, Ltd. self-produced press filter) to obtain 100 g of a solid part 6-1 and 160 g of a liquid part 6-1. Steam distillation was conducted to 100 g of the obtained solid part 6-1 at distillation temperature of 200° C. to obtain 81 g of hard butter 6-1.

Example 7

200 g of the cake 1-1 obtained by the method of Example 1 was put in a juicer (by Zojirushi Corporation) and crushed. Then, 40 g of 31.7° C. liquid ethyl stearate was added thereto and mixed, and solid-liquid separation was conducted to it by pressure filtration (compression pressure 3.3 $kgf/cm^2$; use of The Nisshin OilliO Group, Ltd. self-produced press filter) to obtain 96 g of a solid part 7-1 and 144 g of a liquid part 7-1. Steam distillation was conducted to 96 g of the obtained solid part 7-1 at distillation temperature of 200° C. to obtain 80 g of hard butter 7-1.

Example 8

200 g of the cake 1-1 obtained by the method of Example 1 was put in a juicer (by Zojirushi Corporation) and crushed. Then, solid-liquid separation was conducted to it by pressure filtration (compression pressure 3.3 $kgf/cm^2$; use of The Nisshin OilliO Group, Ltd. self-produced press filter) to obtain 66 g of a solid part 8-1 and 134 g of a liquid part 8-1.

The results are shown in Tables 10 and 11.

TABLE 10

| Flowability of the cake before pressure filtration | | | |
|---|---|---|---|
| | Example 6 | Example 7 | Example 8 |
| flowability | ◎ | ○ | Δ |

◎: Flowability is extremely high; almost liquid form.

○: Having flowability.

Δ: Having flowability to some extent.

X: No flowability.

TABLE 11

| TAG composition | | | | | | | | |
|---|---|---|---|---|---|---|---|---|
| | Example 6 | | | Example 7 | | | Example 8 | |
| TAG composition (%) | Solid part 6-1 | Liquid part 6-1 | Hard butter 6-1 | Solid part 7-1 | Liquid part 7-1 | Hard butter 7-1 | Solid part 8-1 | Liquid part 8-1 |
| $S_2$ | tr | tr | tr | tr | tr | tr | tr | tr |
| POS | 4.2 | 2.3 | 4.2 | 4.3 | 2.4 | 4.3 | 4.0 | 2.4 |
| $PO_2$ | 0.1 | 2.9 | 0.1 | 0.2 | 2.1 | 0.2 | 0.8 | 2.2 |
| $S_3$ | Tr | tr | tr | tr | tr | tr | tr | tr |
| $S_2O$ | 93.0 | 11.5 | 93.0 | 85.3 | 15.8 | 85.3 | 75.2 | 15.8 |
| $SO_2$ | 1.3 | 54.5 | 1.3 | 5.8 | 56.6 | 5.8 | 12.4 | 56.7 |
| $S_2L$ | 0.9 | 3.5 | 0.9 | 2.0 | 3.6 | 2.0 | 2.8 | 3.4 |
| $O_3$ | 0.3 | 12.2 | 0.3 | 1.4 | 11.4 | 1.4 | 2.5 | 11.3 |
| SOL | 0.1 | 10.8 | 0.1 | 0.4 | 6.7 | 0.4 | 1.0 | 6.8 |
| others | 0.1 | 2.3 | 0.1 | 0.6 | 1.4 | 0.6 | 1.3 | 1.4 |
| Fatty acid ethyl content (%) | 13.1 | 37.6 | ND | 11.6 | 29.6 | ND | 3.3 | 8.4 |

Note 1)
TAG composition indicates the composition of each triglyceride in all triglycerides.
P: palmitic acid residue, S: stearic acid residue, O: oleic acid residue, L: linoleic acid residue, and tr: trace.
Note 2)
The content of a fatty acid ethyl indicates a mass % of a fatty acid ethyl in all components.

Example 9

100 g of ethyl palmitate (trade name: Ethyl palmitate, by Inoue Perfumery MFG. Co., Ltd.) was mixed with 900 g of palm olein (produced by INTERCONTINENTAL SPECIALTY FATS SDN BHD, iodine value 56) to obtain 1000 g of a crystallization raw material 9-1. After 1000 g of the obtained crystallization raw material 9-1 was completely dissolved at 50° C., it was cooled down with stirring at 10° C. for 3 hours. Then, solid-liquid separation was conducted to it by pressure filtration (pressure filtration 1: compression pressure 7 $kgf/cm^2$; use of The Nisshin OilliO Group, Ltd. self-produced press filter) to obtain 22 g of a solid part 9-1 and 958 g of a liquid part 9-1. Then, 940 g of the obtained liquid part 9-1 was gradually cooled down with stirring to 5° C., and solid-liquid separation was conducted to it by pressure filtration (pressure filtration 2:compression pressure 30 $kgf/cm^2$; use of The Nisshin OilliO Group, Ltd. self-produced press filter) to obtain 414 g of a solid part 9-2 and 507 g of a liquid part 9-2 (Tables 12 and 13).

TABLE 12

| Flowability before pressure filtration | | |
|---|---|---|
| | Example 9 | |
| | Press. filt. 1 | Press. filt. 2 |
| flowability | ◎◎ | ◎◎ |

◎◎: Liquid form.
◎: Flowability is extremely high; almost liquid form, and easily filterable.

TABLE 13

| Composition analysis results | | | | | | |
|---|---|---|---|---|---|---|
| | Example 9 | | | | | |
| TAG composition (%) Note 1) | Palm olein | Crystal. RM 9-1 | Solid part 9-1 | Liquid part 9-1 | Solid part 9-2 | Liquid part 9-2 |
| $MP_2$ | 0.2 | 0.2 | 2.8 | 0.1 | 0.2 | tr |
| $M_2O$ | 0.2 | 0.2 | 0.2 | 0.2 | 0.3 | 0.1 |
| $P_3$ | 0.6 | 0.6 | 16.2 | 0.2 | 0.4 | tr |
| MPO | 2.1 | 2.1 | 2.1 | 2.1 | 2.8 | 1.5 |
| MPL | 0.6 | 0.6 | 0.6 | 0.6 | 0.5 | 0.7 |
| $P_2S$ | Tr | tr | tr | tr | tr | tr |
| $P_2O$ | 32.6 | 32.6 | 32.6 | 32.6 | 62.0 | 7.2 |
| $P_2L$ | 9.9 | 9.9 | 9.9 | 9.9 | 7.7 | 11.8 |
| $PS_2$ | Tr | tr | tr | tr | tr | tr |
| POS | 5.7 | 5.7 | 5.7 | 5.7 | 11.0 | 1.1 |
| $PO_2$ | 25.7 | 25.7 | 17.0 | 25.9 | 6.1 | 43.0 |
| POL | 9.4 | 9.4 | 0.7 | 9.6 | 0.8 | 17.2 |
| $PL_2$ | 2.0 | 2.0 | 2.0 | 2.0 | 0.6 | 3.2 |
| $S_2O$ | 0.6 | 0.6 | 0.6 | 0.6 | 1.3 | tr |
| $SO_2$ | 2.5 | 2.5 | 2.5 | 2.5 | 1.3 | 3.5 |
| $O_3$ | 3.4 | 3.4 | 3.4 | 3.4 | 1.3 | 5.2 |
| SOL | 1.1 | 1.1 | 1.1 | 1.1 | 0.3 | 1.8 |
| $O_2L$ | 1.6 | 1.6 | 1.6 | 1.6 | 0.6 | 2.5 |
| $OL_2$ | 0.5 | 0.5 | 0.5 | 0.5 | 0.2 | 0.8 |
| others | 1.3 | 1.3 | 0.4 | 1.4 | 2.6 | 0.4 |
| XOX/(XXO + OXX) | 90/10 | — | 90/10 | 90/10 | 94/6 | — |
| Fatty acid ethyl content (%) Note 3) | — | 10.0 | 7.8 | 10.1 | 7.3 | 12.2 |

Note 1)
TAG composition indicates the composition of each triglyceride in all triglycerides.
XOX/(XXO + OXX) indicates a ratio of a triglyceride having a saturated fatty acid residue on each of the first and third positions and a triglyceride having a saturated fatty acid residue on the second position among triglycerides having two saturated fatty acid residues and one oleoyl group.
P: palmitic acid residue, S: stearic acid residue, O: oleic acid residue, L: linoleic acid residue, and tr: trace.
Note 2)
The content of a fatty acid ethyl indicates a mass % of a fatty acid ethyl in all components.

Example 10

50 g of ethyl palmitate (trade name: Ethyl palmitate, by Inoue Perfumery MFG. Co., Ltd.) was mixed with 950 g of palm olein (produced by INTERCONTINENTAL SPECIALTY FATS SDN BHD, iodine value 65) to obtain 1000 g of a crystallization raw material 10-1. After 1000 g of the obtained crystallization raw material 10-1 was completely dissolved at 50° C., it was gradually cooled down with stirring to −5° C., and solid-liquid separation was conducted to it by pressure filtration (pressure filtration 1:compression pressure 30 $kgf/cm^2$; use of The Nisshin OilliO Group, Ltd. self-produced press filter) to obtain 196 g of a solid part 10-1 and 784 g of a liquid part 10-1 (Tables 14 and 15).

TABLE 14

| Flowability before pressure filtration | |
|---|---|
| | Example 10 Press. filt. 1 |
| flowability | ◎◎ |

◎◎: Liquid form.
◎: Flowability is extremely high; almost liquid form, and easily filterable.

TABLE 15

| Composition analysis results | | | | |
|---|---|---|---|---|
| TAG | Example 10 | | | |
| composition (%) Note 1) | Palmolein | Crystal. RM 10-1 | Solid part 10-1 | Liquid part 10-1 |
| $MP_2$ | tr | tr | tr | tr |
| $M_2O$ | 0.1 | 0.1 | 0.5 | tr |
| $P_3$ | tr | tr | tr | tr |
| MPO | 1.8 | 1.8 | 5.6 | 0.8 |
| MPL | 0.7 | 0.7 | 1.5 | 0.5 |
| $P_2S$ | tr | tr | tr | tr |
| $P_2O$ | 16.7 | 16.7 | 67.1 | 3.5 |
| $P_2L$ | 10.7 | 10.7 | 3.8 | 12.5 |
| $PS_2$ | tr | tr | tr | tr |
| POS | 3.1 | 3.1 | 13.0 | 0.5 |
| $PO_2$ | 36.5 | 36.5 | 4.1 | 45.0 |
| POL | 13.5 | 13.5 | 0.9 | 16.8 |
| $PL_2$ | 2.8 | 2.8 | 0.1 | 3.5 |
| $S_2O$ | 0.3 | 0.3 | 1.4 | tr |
| $SO_2$ | 3.5 | 3.5 | 0.3 | 4.4 |
| $O_3$ | 5.1 | 5.1 | 0.3 | 6.4 |
| SOL | 1.5 | 1.5 | 0.2 | 1.9 |
| $O_2L$ | 2.5 | 2.5 | 0.1 | 3.1 |
| $OL_2$ | 0.7 | 0.7 | tr | 0.9 |
| others | 0.5 | 0.5 | 1.1 | 0.4 |
| XOX/(XXO + OXX) | 80/20 | — | 90/10 | — |
| XX-DAG content | 0.3 | 0.3 | 0.7 | 0.2 |
| Fatty acid ethyl content (%) Note 3) | — | 5.0 | 6.0 | 1.4 |

Note 1)
TAG composition indicates the composition of each triglyceride in all triglycerides.
XOX/(XXO + OXX) indicates a ratio of a triglyceride having a saturated fatty acid residue on each of the first and third positions and a triglyceride having a saturated fatty acid residue on the second position among triglycerides having two saturated fatty acid residues and one oleoyl group.
P: palmitic acid residue,
S: stearic acid residue,
O: oleic acid residue,
L: linoleic acid residue, and
tr: trace.
Note 2)
XX-DAG content indicates a mass % of disaturated glycerol in all components. The content was measured by GLC.
Note 3)
The content of a fatty acid ethyl indicates a mass % of a fatty acid ethyl in all components.

Example 11

9000 g of ethyl stearate (trade name: Ethyl Stearate, by Inoue Perfumery MFG. Co., Ltd.) was mixed with 6000 g of high-oleic sunflower oil (trade name: Olein Rich, by Showa Sangyo Co., Ltd.). 0.3 mass % of the powdered lipase composition 1 was added thereto, and stirred at 40° C. for 20 hours. An enzyme powder was removed by filtration to obtain 14700 g of a reactant 11-1. Thin-film distillation was conducted to 14500 g of the obtained reactant 11-1, and a fatty acid ethyl was removed from the reactant at distillation temperature of 140° C. to obtain 5795 g of a distillation residue 11-1 wherein the content of a fatty acid ethyl is 3.5 mass % (Table X1).

906 g of a distillate 11-1 was mixed with 5000 g of the obtained distillation residue 11-1 to obtain 5906 g of a crystallization raw material 11-1 wherein the content of a fatty acid ethyl is 18.3 mass %. After 2001 g of the obtained crystallization raw material 11-1 was completely dissolved at 50° C., it was cooled down with stirring at 27° C. for 3 hours. Then, solid-liquid separation was conducted to it by pressure filtration (pressure filtration 1:compression pressure 7 kgf/cm$^2$; use of The Nisshin OilliO Group, Ltd. self-produced press filter) to obtain 450 g of a solid part 11-1 and 1904 g of a liquid part 11-1 (Tables 16 and 17). Thin-film distillation was conducted to 1845 g of the obtained liquid part 11-1, and a fatty acid ethyl was removed from the reactant at distillation temperature of 140° C. to obtain 1389 g of a distillation residue 11-2 wherein the content of a fatty acid ethyl is 5.2 mass %. Steam distillation was conducted to 1351 g of the obtained distillation residue 11-2 at distillation temperature of 200° C. Then, a fatty acid ethyl was removed to obtain 1227 g of a distillation residue 11-3 wherein the content of a fatty acid ethyl is a trace amount %. 4788 g of acetone was added to 1197 g of the obtained distillation residue 11-3, dissolved, and cooled down to 5° C. The obtained solid part was separated by filtration to obtain 555 g of a solid part 11-2 and 651 g of a liquid part 11-2. Acetone was removed from 530 g of the obtained solid part 11-2, and the residue was purified by the book to obtain 500 g of hard butter 11-1 (Tables 18 and 19).

TABLE 16

| Flowability before pressure filtration | |
|---|---|
| | Example 11 Bfr. Press. filt. 1 |
| flowability | ◎◎ |

◎◎: Liquid form.
◎: Flowability is extremely high; almost liquid form, and easily filterable.

TABLE 17

| Composition analysis results | | | | | | | |
|---|---|---|---|---|---|---|---|
| | Example 11 | | | | | | |
| TAG composition (%) Note 1) | Reactant 11-1 | Distill. residue 11-1 | Crystal. RM 11-1 | Solid part 11-1 | Liquid part 11-1 | Distill. residue 11-2 | Distill. residue 11-3 |
| $PS_2$ | 0.2 | 0.2 | 0.2 | 1.7 | tr | tr | tr |
| POS | 3.0 | 3.0 | 3.0 | 3.1 | 3.0 | 3.0 | 3.0 |
| $PO_2$ | 1.5 | 1.5 | 1.5 | 1.0 | 1.4 | 1.4 | 1.4 |
| $S_3$ | 1.0 | 1.0 | 1.0 | 15.8 | 0.4 | 0.4 | 0.4 |
| $S_2O$ | 43.7 | 43.7 | 43.7 | 45.0 | 43.5 | 43.5 | 43.5 |
| $SO_2$ | 35.2 | 35.2 | 35.2 | 24.3 | 35.3 | 35.3 | 35.3 |
| $S_2L$ | 2.4 | 2.4 | 2.4 | 1.2 | 2.5 | 2.5 | 2.5 |
| $O_3$ | 7.3 | 7.3 | 7.3 | 5.6 | 7.4 | 7.4 | 7.4 |
| SOL | 3.9 | 3.9 | 3.9 | 2.3 | 3.8 | 3.8 | 3.8 |
| others | 1.8 | 1.8 | 1.8 | 0.2 | 2.7 | 2.7 | 2.7 |
| SS-DAG content (%) Note 2) | 0.4 | 0.9 | 1.0 | 33.0 | 0.1 | 0.1 | 0.1 |
| XOX/(XXO + OXX) | 99/1 | 99/1 | 99/1 | — | 99/1 | 99/1 | 99/1 |
| Fatty acid ethyl content (%) Note 3) | — | 3.5 | 18.3 | 12.0 | 18.4 | 5.2 | tr |

TABLE 18

| Composition analysis results | | | |
|---|---|---|---|
| | Example 11 | | |
| TAG composition (%) Note 1) | Solid part 11-2 | Liquid part 11-2 | Hard butter 11-1 |
| $PS_2$ | 0.2 | tr | 0.2 |
| POS | 4.4 | 1.5 | 4.4 |
| $PO_2$ | tr | 2.9 | tr |
| $S_3$ | 0.9 | tr | 0.9 |
| $S_2O$ | 85.9 | 1.9 | 85.9 |
| $SO_2$ | 3.9 | 64.9 | 3.9 |
| $S_2L$ | 3.5 | 3.4 | 3.5 |
| $O_3$ | tr | 14.5 | tr |
| SOL | tr | 7.9 | tr |
| others | 1.2 | 3.0 | 1.2 |
| SS-DAG content (%) Note 2) | 0.6 | tr | 0.6 |
| XOX/(XXO + OXX) | 99/1 | — | 99/1 |
| Fatty acid ethyl content (%) Note 3) | tr | tr | ND |

Note 1)
TAG composition indicates the composition of each triglyceride in all triglycerides.
XOX/(XXO + OXX) indicates a ratio of a triglyceride having a saturated fatty acid residue on each of the first and third positions and a triglyceride having a saturated fatty acid residue on the second position among triglycerides having two saturated fatty acid residues and one oleoyl group.
P: palmitic acid residue,
S: stearic acid residue,
O: oleic acid residue,
L: linoleic acid residue, and
tr: trace.
Note 2)
SS-DAG content indicates a mass % of distearoyl glycerol in all components. The content was measured by GLC.
Note 3)
The content of a fatty acid ethyl indicates a mass % of a fatty acid ethyl in all components.

Example 12

Sample chocolates were produced using the above hard butter 11-1 by the method comprising the steps of mixing, refining and conching them with the following devices in accordance with the blending quantity of Table 19, and tempering them from 50° C. to 29° C. then to 32° C. Then, each sample was evaluated.

There was no problem with viscosity as manufactured or demoulding. The obtained chocolates were preserved at 20° C. for one week, and ease of snapping, gloss, and the melting in the mouth were evaluated. As a result, a chocolate 1 in which hard butter 11-1 was used melted well in the mouth and easily snapped.

(Devices Used for Producing Sample Chocolates)
Mixing: a versatile mixer (5DM-L, by Dalton Co., Ltd.)
Refining: a three roller mill (SDY300, by Buglers)
Conching: a versatile mixer (5DM-L, by Dalton Co., Ltd.)

TABLE 19

| Blending quantity of chocolates (mass %) | | |
|---|---|---|
| | Control chocolate 1 | Chocolate 1 |
| sugar | 47.45 | 47.45 |
| cacao mass | 40.0 | 40.0 |
| *(cacao butter ratio) | (22.0) | (22.0) |
| cacao butter | 12.0 | — |
| hard butter 11-1 | — | 4.4 |
| Palm Mid Fraction | — | 7.6 |
| lecithin | | |
| flavoring agent | 0.5 | 0.5 |
| | 0.05 | 0.05 |

(Chocolate Evaluation Results)

Chocolates produced by the above method were evaluated in respect of ease of demoulding, ease of snapping, gloss, and the melting in the mouth. The evaluation results are shown in Table 20.

TABLE 20

| Evaluation results of chocolate bars | | |
|---|---|---|
| | Control chocolate 1 | Chocolate 1 |
| snapping | ○ | ○ |
| melting in the mouth | ○ | ○ |
| demoulding | ◎ | ◎ |
| gloss | ◎ | ◎ |

Evaluation was further conducted in accordance with the sensory test by 10 panelists. The criteria are as follows:

<Criteria>

| | |
|---|---|
| Ease of snapping | ◎: having extremely good snapping<br>○: having good snapping<br>Δ: less snapping |

-continued

| | |
|---|---|
| Melting in the mouth | ◎: extremely well melting in the mouth<br>○: well melting in the mouth<br>Δ: poor melting in the mouth |
| Gloss | ◎: extremely good<br>○: good but partially fogging<br>Δ: no gloss |
| Demoulding | ◎: demoulding 15 minutes after cooling<br>○: demoulding 20 minutes after cooling<br>Δ: no demoulding |

Example 13

2400 g of ethyl stearate (trade name: Ethyl Stearate, by Inoue Perfumery MFG. Co., Ltd.) was mixed with 1600 g of high-linoleic safflower oil (by The Nisshin OilliO Group, Ltd.). 0.3 mass % of the powdered lipase composition 1 was added thereto, and stirred at 40° C. for 20 hours. An enzyme powder was removed by filtration to obtain 3920 g of a reactant 13-1. Thin-film distillation was conducted to 3900 g of the obtained reactant 13-1, and a fatty acid ethyl was removed from the reactant at distillation temperature of 140° C. to obtain 1555 g of a distillation residue 13-1 wherein the content of a fatty acid ethyl is 3.7 mass % (Table 22).

261 g of a distillate 13-1 was mixed with 1500 g of the obtained distillation residue 13-1 to obtain 1761 g of a crystallization raw material 13-1 wherein the content of a fatty acid ethyl is 18.0 mass %. After 1700 g of the obtained crystallization raw material 13-1 was completely dissolved at 50° C., it was cooled down with stirring at 23° C. for 3 hours. Then, solid-liquid separation was conducted to it by pressure filtration (pressure filtration 1:compression pressure 7 kgf/$cm^2$; use of The Nisshin OilliO Group, Ltd. self-produced press filter) to obtain 35 g of a solid part 13-1 and 1624 g of a liquid part 13-1. Then, 1600 g of the obtained liquid part 13-1 was gradually cooled down with stirring to 10° C., and solid-liquid separation was conducted to it by pressure filtration (pressure filtration 2:compression pressure 30 kgf/$cm^2$; use of The Nisshin OilliO Group, Ltd. self-produced press filter) to obtain 627 g of a solid part 13-2 and 941 g of a liquid part 13-2 (Tables 21 and 22).

TABLE 21

| Flowability before pressure filtration | | |
|---|---|---|
| | Example 13 | |
| | Press. filt. 1 | Press. filt. 2 |
| flowability | ◎◎ | ◎◎ |

◎◎: Liquid form.
◎: Flowability is extremely high; almost liquid form, and easily filterable.

TABLE 22

| Composition analysis results | | | | | | | |
|---|---|---|---|---|---|---|---|
| | Example 13 | | | | | | |
| TAG composition (%) Note 1) | Reactant 13-1 | Distillation residue 13-1 | Crystal. RM 13-1 | Solid part 13-1 | Liquid part 13-1 | Solid part 13-2 | Liquid part 13-2 |
| $P_2L$ | 0.3 | 0.3 | 0.3 | 0.3 | 0.3 | 0.5 | 0.1 |
| $PS_2$ | 0.3 | 0.3 | 0.3 | 5.1 | 0.1 | 0.2 | tr |

TABLE 22-continued

Composition analysis results

| TAG composition (%) Note 1) | Example 13 Reactant 13-1 | Distillation residue 13-1 | Crystal. RM 13-1 | Solid part 13-1 | Liquid part 13-1 | Solid part 13-2 | Liquid part 13-2 |
|---|---|---|---|---|---|---|---|
| POS | 1.2 | 1.2 | 1.2 | 1.2 | 1.2 | 2.0 | 0.6 |
| PLS | 5.8 | 5.8 | 5.8 | 5.8 | 5.8 | 7.0 | 4.9 |
| PLO | 0.7 | 0.7 | 0.7 | 0.7 | 0.7 | 0.7 | 0.7 |
| $PL_2$ | 1.6 | 1.6 | 1.6 | 0.2 | 1.6 | tr | 2.8 |
| $S_3$ | 0.7 | 0.7 | 0.7 | 11.7 | 0.3 | 0.7 | tr |
| $S_2O$ | 7.8 | 7.8 | 7.8 | 7.8 | 7.8 | 14.0 | 3.0 |
| $S_2L$ | 39.9 | 39.9 | 39.9 | 39.9 | 39.9 | 67.0 | 19.1 |
| SLO | 10.5 | 10.5 | 10.5 | 6.9 | 10.6 | 2.1 | 17.1 |
| $SL_2$ | 24.8 | 24.8 | 24.8 | 19.8 | 24.9 | 5.2 | 40.0 |
| $OL_2$ | 2.3 | 2.3 | 2.3 | 0.4 | 2.4 | tr | 4.2 |
| $L_3$ | 3.9 | 3.9 | 3.9 | 0.1 | 4.0 | Tr | 7.1 |
| others | 0.2 | 0.2 | 0.2 | 0.1 | 0.4 | 0.6 | 0.4 |
| SS-DAG content (%) Note 2) | 0.5 | 1.1 | 1.0 | 16.5 | 0.1 | 0.4 | tr |
| Fatty acid ethyl content (%) Note 3) | — | 3.7 | 18.0 | 14.1 | 18.1 | 11.0 | 22.7 |

Note 1)

TAG composition indicates the composition of each triglyceride in all triglycerides.

XOX/(XXO + OXX) indicates a ratio of a triglyceride having a saturated fatty acid residue on each of the first and third positions and a triglyceride having a saturated fatty acid residue on the second position among triglycerides having two saturated fatty acid residues and one oleoyl group.

P: palmitic acid residue, S: stearic acid residue, O: oleic acid residue, L: linoleic acid residue, and tr: trace.

Note 2)

SS-DAG content indicates a mass % of distearoyl glycerol in all components. The content was measured by GLC.

Note 3)

The content of a fatty acid ethyl indicates a mass % of a fatty acid ethyl in all components.

Example 14

320 g of high-oleic sunflower oil (trade name: Olein Rich, by Showa Sangyo Co., Ltd.), 380 g of Palm Mid Fraction (by INTERCONTINENTAL SPECIALTY FATS SDN BHD, iodine value 45), 180 g of ethyl stearate (trade name: Ethyl Stearate, by Inoue Perfumery MFG. Co., Ltd.), and 120 g of ethyl palmitate (trade name: Ethyl palmitate, by Inoue Perfumery MFG. Co., Ltd.) was mixed. 0.5 mass % of the powdered lipase composition 1 was added thereto, and stirred at 50° C. for 16 hours. An enzyme powder was removed by filtration to obtain 997 g of a reactant 14-1.

After 997 g of the obtained reactant 14-1 was completely dissolved at 50° C., it was cooled down with stirring at 23° C. for 3 hours. Then, solid-liquid separation was conducted to it by filtration under reduced pressure to obtain 168 g of a solid part 14-1 and 805 g of a liquid part 14-1. Then, 805 g of the obtained liquid part 14-1 was gradually cooled down with stirring to 12.5° C., and solid-liquid separation was conducted to it by pressure filtration (pressure filtration 1:compression pressure 30 kgf/cm$^2$; use of The Nisshin OilliO Group, Ltd. self-produced press filter) to obtain 180 g of a solid part 14-2 and 632 g of a liquid part 14-2 (Table 23). Steam distillation was conducted to the obtained solid part 14-2 at distillation temperature of 200° C., and, a fatty acid ethyl was removed. Then, it was purified by the book to obtain hard butter 14-1.

TABLE 23

Composition analysis results

| TAG composition (%) Note 1) | Example 14 Reactant 14-1 | Solid part 14-1 | Liquid part 14-1 | Solid part 14-2 | Liquid 14-2 | Hard butter 14-1 |
|---|---|---|---|---|---|---|
| $P_3$ | 1.3 | 5.1 | 0.2 | 0.4 | 0.2 | 0.3 |
| POM | 0.6 | 0.5 | 0.5 | 0.3 | 0.7 | 0.3 |
| $P_2S$ | 1.8 | 8.1 | 0.1 | 0.4 | tr | 0.4 |
| $P_2O$ | 17.3 | 15.0 | 17.3 | 22.4 | 14.6 | 22.5 |
| $P_2L$ | 2.5 | 1.3 | 2.5 | 0.8 | 3.3 | 0.8 |
| $PS_2$ | 0.9 | 4.2 | tr | 0.1 | tr | 0.1 |
| POS | 21.9 | 22.4 | 21.6 | 44.1 | 10.1 | 44.0 |
| $PO_2$ | 16.6 | 12.4 | 19.1 | 3.3 | 30.0 | 3.3 |
| PLS | 4.2 | 2.6 | 3.2 | 2.0 | tr | 2.0 |
| POL | 3.9 | 2.5 | 4.0 | 0.4 | 5.9 | 0.4 |
| $S_3$ | tr | 0.8 | tr | tr | tr | tr |
| $S_2O$ | 7.5 | 9.2 | 7.3 | 19.8 | 1.2 | 19.9 |

TABLE 23-continued

| Composition analysis results | | | | | | |
|---|---|---|---|---|---|---|
| | Example 14 | | | | | |
| TAG composition (%) Note 1) | Reactant 14-1 | Solid part 14-1 | Liquid part 14-1 | Solid part 14-2 | Liquid 14-2 | Hard butter 14-1 |
| $SO_2 + S_2L$ | 13.1 | 9.7 | 14.4 | 4.6 | 18.4 | 4.6 |
| $O_3$ | 5.1 | 3.9 | 5.7 | 0.7 | 7.7 | 0.6 |
| SOL | 2.5 | 1.7 | 2.8 | 0.5 | 5.2 | 0.5 |
| others | 0.8 | 0.6 | 1.3 | 0.2 | 2.7 | 0.3 |
| XOX/ (XXO + OXX) | 99/1 | 99/1 | 99/1 | — | 99/1 | 99/1 |
| Fatty acid ethyl content (%) Note 2) | 30.0 | 22.7 | 31.9 | 14.4 | 30.4 | tr |

Note 1)
TAG composition indicates the composition of each triglyceride in all triglycerides.
XOX/(XXO + OXX) indicates a ratio of a triglyceride having a saturated fatty acid residue on each of the first and third positions and a triglyceride having a saturated fatty acid residue on the second position among triglycerides having two saturated fatty acid residues and one oleoyl group.
P: palmitic acid residue, S: stearic acid residue, O: oleic acid residue, L: linoleic acid residue, and tr: trace.
Note 2)
The content of a fatty acid ethyl indicates a mass % of a fatty acid ethyl in all components.

What is claimed is:

1. A method of producing triglycerides rich in XOX fat, which comprises the steps of heating and dissolving triglycerides (XOX fat) which comprise 20 to 60 mass % of a triglyceride having a saturated fatty acid residue on each of the first and third positions and an oleoyl group on the second position in total triglycerides in the presence of 1 to 30 mass % of a fatty acid lower alkyl ester;

and then cooling the mixture to precipitate crystals and conducting solid-liquid separation.

2. The method according to claim 1, wherein the triglycerides which comprise 20 to 60 mass % of the XOX fat in total triglycerides are a distillation residue obtained by transesterifying a triglyceride having an oleoyl group on the second position with a fatty acid lower alkyl ester and then distilling the resultant.

3. The method according to claim 1, wherein the saturated fatty acid residue on each of the first and third positions is a saturated fatty acid residue having 16 to 22 carbon atoms.

4. The method according to claim 1, which comprises the steps of heating and dissolving the triglycerides which comprise 20 to 60 mass % of the XOX fat in total triglycerides in the presence of 1 to 30 mass % of a fatty acid lower alkyl ester; and then cooling the mixture with stirring to precipitate crystals and conducting solid-liquid separation.

5. The method according to claim 1, wherein the triglycerides comprise 30 to 60 mass % of the XOX fat in total triglycerides.

6. A method of producing triglycerides rich in XLX fat, which comprises the steps of heating and dissolving triglycerides which comprise 20 to 60 mass % of a triglyceride (XLX fat) having a saturated fatty acid residue on each of the first and third positions and a linoleoyl group on the second position in total triglycerides in the presence of 1 to 30 mass % of a fatty acid lower alkyl ester;

and then cooling the mixture to precipitate crystals and conducting solid-liquid separation.

7. A method of producing triglycerides wherein the concentration of XOX fat and/or XLX fat is further increased, which comprises the steps of adding 1 to 50 parts by weight of a fatty acid lower alkyl ester per 100 parts by weight of the crystals before the solid-liquid separation in the production method according to claim 1, and crushing the mixture; or crushing said crystals and then adding said fatty acid lower alkyl ester thereto; and then filtering the mixture by compressing to obtain a solid content.

8. A method of producing triglycerides wherein the concentration of XOX fat and/or XLX fat is increased, which comprises the steps of crushing solid triglycerides rich in XOX fat and/or XLX fat after adding thereto 1 to 50 parts by weight of a fatty acid lower alkyl ester per 100 parts by weight of said solid triglycerides; or crushing the triglycerides and adding said fatty acid lower alkyl ester thereto; and then filtering the mixture by compressing to obtain a solid content.

9. A method of producing fats and oils wherein the concentration of XXX fat and/or XX diglyceride is decreased, which comprises the steps of heating and dissolving triglycerides which comprise 20 to 60 mass % of XOX fat and/or XLX fat in total triglycerides in the presence of 1 to 30 mass % of a fatty acid lower alkyl ester; and then cooling the mixture and removing by crystallization a triglyceride (XXX fat) which consists of saturated fatty acid residues only and/or a diglyceride (XX) which consist of saturated fatty acid residues only.

10. The method according to any claim 1, which comprises the steps of heating and dissolving triglycerides which comprise 20 to 60 mass % of XOX fat and/or XLX fat in total triglycerides in the presence of 1 to 30 mass % of a fatty acid lower alkyl ester; then cooling the mixture and removing by crystallization a triglyceride (XXX fat) which consists of saturated fatty acid residues only and/or a diglyceride (XX) which consist of saturated fatty acid residues only; and further cooling the reactant with stirring to crystallize XOX fat and/or XLX fat, and conducting solid-liquid separation.

11. The method according to claim 1, which comprises the steps of heating and dissolving triglycerides which comprise 20 to 60 mass % of XOX fat and/or XLX fat in total triglycerides in the presence of 1 to 30 mass % of a fatty acid lower alkyl ester; then cooling the mixture and removing by crystallization a triglyceride (XXX fat) which consists of saturated fatty acid residues only and/or a diglyceride (XX) which consist of saturated fatty acid residues only; and further fractionating the reactant with a solvent(s) to crystallize XOX fat and/or XLX fat, and conducting solid-liquid separation.

12. The method according to claim 1 which comprises the step of purifying the obtained solid content.

* * * * *